United States Patent
Vajaria et al.

(10) Patent No.: US 9,734,568 B2
(45) Date of Patent: Aug. 15, 2017

(54) AUTOMATED INLINE INSPECTION AND METROLOGY USING SHADOW-GRAM IMAGES

(71) Applicant: KLA-TENCOR CORPORATION, Milpitas, CA (US)

(72) Inventors: Himanshu Vajaria, San Jose, CA (US); Sina Jahanbin, San Jose, CA (US); Bradley Ries, San Jose, CA (US); Mohan Mahadevan, Santa Clara, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 14/630,252

(22) Filed: Feb. 24, 2015

(65) Prior Publication Data

US 2015/0243018 A1    Aug. 27, 2015

Related U.S. Application Data

(60) Provisional application No. 61/944,244, filed on Feb. 25, 2014.

(51) Int. Cl.
| | |
|---|---|
| *G06K 9/00* | (2006.01) |
| *G06T 7/00* | (2017.01) |
| *G01N 21/95* | (2006.01) |
| *G06K 9/48* | (2006.01) |
| *G06K 9/62* | (2006.01) |

(Continued)

(52) U.S. Cl.
CPC ....... *G06T 7/0004* (2013.01); *G01N 21/9503* (2013.01); *G06K 9/481* (2013.01); *G06K 9/6204* (2013.01); *G06T 7/13* (2017.01); *G06T 7/62* (2017.01); *G06K 2209/19* (2013.01); *G06T 2207/10024* (2013.01); *G06T 2207/30148* (2013.01)

(58) Field of Classification Search
CPC .................................................... G06T 7/0004
See application file for complete search history.

(56) References Cited

U.S. PATENT DOCUMENTS

| | | |
|---|---|---|
| 6,201,240 B1 | 3/2001 | Dotan et al. |
| 8,818,074 B2 | 8/2014 | Pai et al. |
(Continued)

FOREIGN PATENT DOCUMENTS

| | | |
|---|---|---|
| EP | 2191229 B1 | 7/2011 |
| KR | 10-2013-0095211 A | 8/2013 |

OTHER PUBLICATIONS

International Search Report, PCT/US2015/017549, ISA/KR, Sep. 3, 2015.

*Primary Examiner* — Oneal R Mistry
(74) *Attorney, Agent, or Firm* — Hodgson Russ LLP (57) ABSTRACT

Shadow-grams are used for edge inspection and metrology of a stacked wafer. The system includes a light source that directs collimated light at an edge of the stacked wafer, a detector opposite the light source, and a controller connected to the detector. The stacked wafer can rotate with respect to the light source. The controller analyzes a shadow-gram image of the edge of the stacked wafer. Measurements of a silhouette of the stacked wafer in the shadow-gram image are compared to predetermined measurements. Multiple shadow-gram images at different points along the edge of the stacked wafer can be aggregated and analyzed.

15 Claims, 8 Drawing Sheets

(51) Int. Cl.
    *G06T 7/13*         (2017.01)
    *G06T 7/62*         (2017.01)

(56) References Cited

U.S. PATENT DOCUMENTS

| | | | |
|---|---|---|---|
| 2002/0072133 A1* | 6/2002 | Jun | G06T 7/0004 438/14 |
| 2004/0207836 A1 | 10/2004 | Chhibber | |
| 2005/0280807 A1* | 12/2005 | Backhauss | G01N 21/9503 356/237.2 |
| 2006/0109484 A1 | 5/2006 | Akamatsu | |
| 2007/0127807 A1* | 6/2007 | Koshikawa | G06K 9/00 382/149 |
| 2007/0237385 A1* | 10/2007 | Kato | G01N 21/9501 382/149 |
| 2008/0002877 A1 | 1/2008 | Simpkins | |
| 2009/0116726 A1* | 5/2009 | Postolov | G01N 21/9501 382/145 |
| 2009/0142916 A1 | 6/2009 | Prenz et al. | |
| 2009/0316978 A1* | 12/2009 | Fujimori | G01B 11/2518 382/144 |
| 2010/0134615 A1* | 6/2010 | Akamatsu | G01B 11/2433 348/135 |
| 2010/0295934 A1* | 11/2010 | Okamoto | G01N 21/9503 348/87 |
| 2011/0054659 A1* | 3/2011 | Carlson | G01N 21/9501 700/109 |
| 2012/0086796 A1* | 4/2012 | Lewis | G01N 21/956 348/87 |
| 2013/0100441 A1 | 4/2013 | Tagawa et al. | |
| 2013/0215258 A1 | 8/2013 | Gaglin et al. | |

\* cited by examiner

AUTOMATED INLINE INSPECTION AND METROLOGY USING SHADOW-GRAM IMAGES

CROSS-REFERENCE TO RELATED APPLICATIONS

This application claims priority to the provisional patent application filed Feb. 25, 2014 and assigned U.S. App. No. 61/944,244, the disclosure of which is hereby incorporated by reference.

FIELD OF THE DISCLOSURE

This disclosure relates to inspection and metrology using shadow-gram images and, more particularly, inspection and metrology of stacked wafers using shadow-gram images.

BACKGROUND OF THE DISCLOSURE

Stacked (or bonded) wafers are frequently used in the semiconductor industry. One or more ultrathin wafers bonded to a carrier wafer is an example of a stacked wafer, though other semiconductor wafer designs also can be stacked wafers. For example, a stacked wafer can include a device wafer bonded to a carrier wafer. These stacked wafers can be used for both memory and logic applications. Three-dimensional integrated circuits ("3D IC") can be produced using stacked wafers.

Stacked wafers can have complex edge profiles. The various layers of a stacked wafer can have different heights and diameters. These dimensions can be affected by the size of the various wafers prior to stacking or by processing steps. Such processing steps also can affect the edge profile of the stacked wafer, potentially even causing an undesirable edge profile.

Stacked wafers with fabrications errors can cause problems during manufacturing. For example, stacked wafers with edge profiles that do not meet specifications can pose a risk during chemical mechanical polishing (CMP), other processing steps, or wafer handling. Centricity of the stacked wafer affects the CMP process or increases handling risks. During CMP, centricity affects placement of the polishing pad with respect to the center of the stacked wafer and subsequent planarization. During wafer handling, the balance of a stacked wafer or clearance within manufacturing equipment can be affected by centricity of the stacked wafer.

Improper centricity can even ruin a stacked wafer or damage manufacturing equipment. If the stacked wafer is undercut, improperly bonded together, or contains too much glue, then the stacked wafer can break within the CMP tool, contaminating or damaging the CMP tool. Such contamination or damage leads to unwanted downtime or can even stop production within a semiconductor fab.

Furthermore, the CMP process can result in undesired edge profiles on a stacked wafer. For example, too much or not enough material may be removed during a CMP process or the CMP process may result in undercuts, overhangs, or whiskers. These undesired edge profiles can affect device yield or can impact later manufacturing steps.

Inspection can be used to identify problems with stacked wafers, but stacked wafers present unique edge inspection challenges. Undercut or other edge profiles of a stacked wafer makes it difficult to obtain scattered or reflected light in an image detector. More complicated edge profiles compound this problem. Jagged edges or complicated edge profiles also can lead to noise. For example, when a stacked wafer is stacked improperly, one side of the device wafer can have an overhang over an edge of the carrier wafer while the other side of the device wafer lies too far inside the carrier wafer. In such a situation, conventional systems can only optimize detection of the overhang or the device wafer that lies too far inside the carrier wafer. Noise and the lack of scattered or reflected light mean that improper stacking cannot be effectively analyzed.

Manual and offline edge profile measurement methods for stacked wafers are slow, time-consuming tools which provide poor quality results. These error-prone techniques can fail to accurately measure or detect flaws in stacked wafers. Furthermore, manual and offline edge profile measurement cannot be used for real-time process control during manufacturing.

There is an increasing need, especially at the back end of line (BEOL), to inspect wafers that are thinned and bonded to carriers. In some cases, these stacked wafers will not have standard edge profile shapes. Furthermore, incorrect stacking of stacked wafers can lead to loss of multiple device wafers if even one stacking step has an error. For example, the cost of one stacking fault in a hybrid memory cubicle could destroy as many as eight fully-processed device wafers.

The current solution for edge metrology is not accurate enough or fast enough for stacked wafers. Furthermore, the current solution for edge metrology may not accurately indicate when the edge profile of a stacked wafer does not match a particular model. Therefore, what is needed is an improved edge inspection technique for stacked wafers.

BRIEF SUMMARY OF THE DISCLOSURE

In a first embodiment, a system is provided. The system has a light source, detector, and controller. The light source is configured to direct collimated light at an edge of a stacked wafer. The detector is disposed opposite the light source and is configured to acquire a shadow-gram image of the edge of the stacked wafer. The controller is operatively connected to the detector. The controller is configured to receive the shadow-gram image and compare characteristics of the shadow-gram image with predetermined measurements to inspect an edge profile of the stacked wafer. The detector can be configured to acquire a plurality of shadow-gram images of different locations of the stacked wafer. The stacked wafer may be configured to rotate with respect to the light source. For example, the system may include a platen configured to rotate the stacked wafer.

In a second embodiment, a non-transitory computer-readable storage medium, comprising one or more programs for executing the following steps on one or more computing devices is provided. The steps include receiving at least one shadow-gram image of an edge of a stacked wafer, detecting an edge of a silhouette of the stacked wafer in the shadow-gram image, determining measurements of the edge of the silhouette based on an image analysis of the shadow-gram image, and comparing measurements of the edge of the silhouette to predetermined measurements. A result of the comparing may be displayed. The detecting can be one of a search-based detection, a zero-crossing based detection, morphological detection, or classification detection. The image analysis of the shadow-gram image can be one or more morphological operations, such as applying a bit mask, and may also include joining edges together using the bit-mask. The predetermined measurements can be at least one of carrier height, device height, inset width, carrier height tolerance, device height tolerance, carrier edge protrusion threshold, and device edge protrusion threshold. The edge of the silhouette may be encoded using a chain code algorithm such that the chain code algorithm creates a pixel matrix. The detecting can be one of a histogram analysis, segmentation analysis, or ray tracing algorithm.

Measurements of the edge of the silhouette at a plurality of locations on the stacked wafer may be aggregated such that information for the stacked wafer is provided. The information for the stacked wafer may be at least one of diameter, center offset, thickness, average total height, average device height, average carrier height, minimum goodness, maximum of all undercut heights, maximum of all undercut widths, maximum of device edge protrusion, maximum of carrier edge protrusion below, and maximum carrier protrusion left.

In a third embodiment, a method is provided. A shadow-gram image of an edge of a stacked wafer is obtained using a detector. Measurements of a silhouette of the stacked wafer in the shadow-gram image are compared to predetermined measurements using a controller. The predetermined measurements can be at least one of carrier height, device height, inset width, carrier height tolerance, device height tolerance, carrier edge protrusion threshold, and device edge protrusion threshold.

The stacked wafer may be rotated and a plurality of the shadow-gram images at different points along the edge of the stacked wafer can be obtained. The measurements of the silhouette in the plurality of shadow-gram images can be aggregated such that information for the stacked wafer is provided. The information for the stacked wafer can be at least one of diameter, center offset, thickness, average total height, average device height, average carrier height, minimum goodness, maximum of all undercut heights, maximum of all undercut widths, maximum of device edge protrusion, maximum of carrier edge protrusion below, and maximum carrier protrusion left.

DESCRIPTION OF THE DRAWINGS

For a fuller understanding of the nature and objects of the disclosure, reference should be made to the following detailed description taken in conjunction with the accompanying drawings, in which.

DETAILED DESCRIPTION OF THE DISCLOSURE

Although claimed subject matter will be described in terms of certain embodiments, other embodiments, including embodiments that do not provide all of the benefits and features set forth herein, are also within the scope of this disclosure. Various structural, logical, process step, and electronic changes may be made without departing from the scope of the disclosure. Accordingly, the scope of the disclosure is defined only by reference to the appended claims.

Embodiments of this disclosure provide metrology measurements, edge inspection, and defect detection for stacked wafers. Metrology can be performed across several points along the edge of the stacked wafer to quantify stacking characteristics such as, for example, concentricity, excess glue, wafer whiskers, undercuts, wafer stacking angles, or other issues. Inspection of irregular wafers can be performed.

Figure 1:
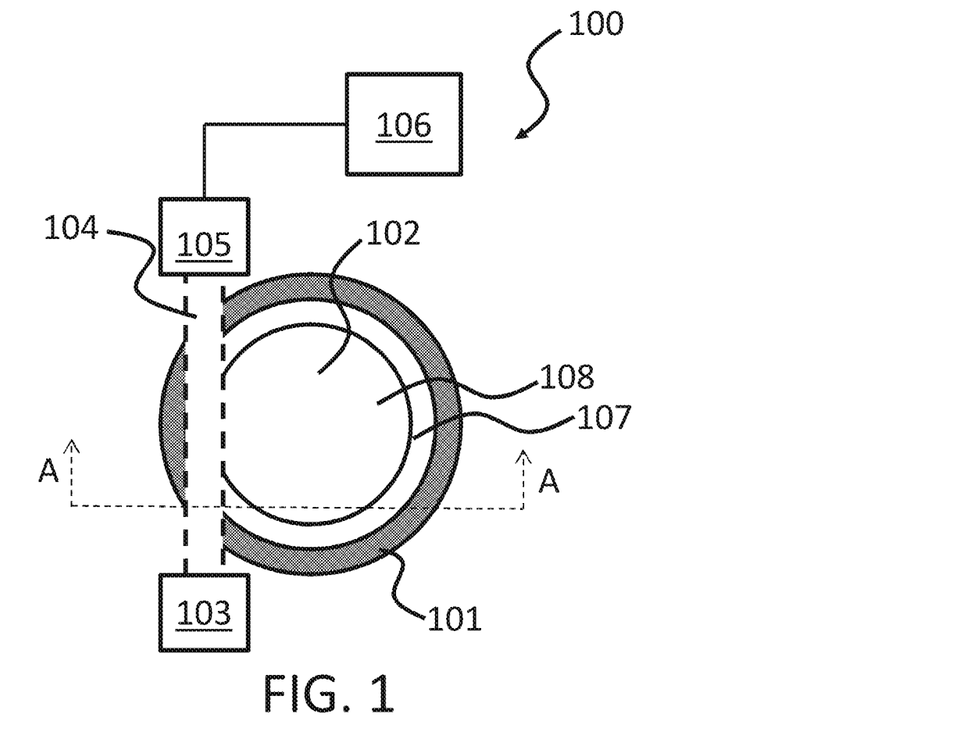
FIGS. 1-2 are a top view and corresponding cross-sectional side view along A-A of a block diagram of a system in accordance with an embodiment of the present disclosure.
Figure 2:
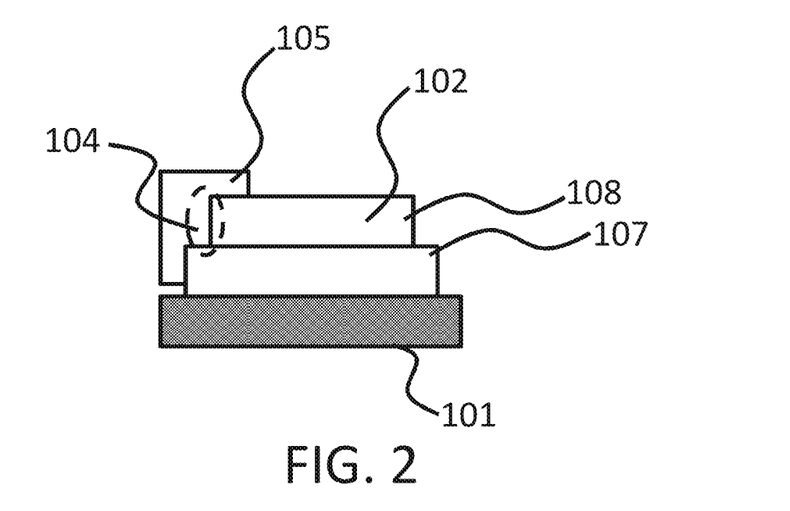
Figure 3:
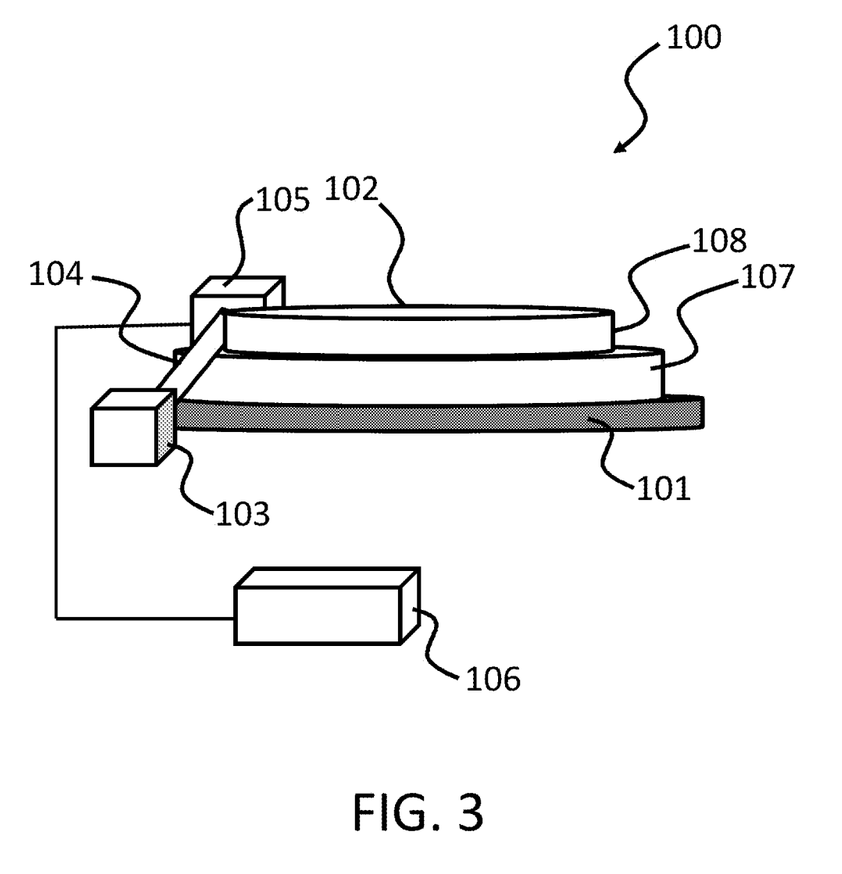
FIG. 3 is a perspective view of a system corresponding to the embodiment of FIGS. 1-2.

FIGS. 1-2 are a top view and corresponding cross-sectional side view along A-A of a block diagram of a system 100 in accordance with an embodiment of the present disclosure. FIG. 3 is a perspective view of a system 100 corresponding to the embodiment of FIGS. 1-2. System 100 is configured to perform edge metrology on stacked wafers by acquiring images that are shadow-grams. A shadow-gram applies a shadowgraph technique and visualizes or images a shadow. A platen 101 can be configured to rotate a stacked wafer 102, though the system 100 also can rotate with respect to the stacked wafer 102. Such rotation can be stepped or continuous. The stacked wafer 102 also may not rotate during inspection and metrology and components of the system 100 may be fixed.

The exemplary stacked wafer 102 is shown with a first layer 107 and a second layer 108. The first layer 107 and second layer 108 may have different diameters, such as those illustrated in FIG. 1. For example, the first layer 107 can be a carrier wafer and the second layer 108 can be a device wafer. Alternatively, the first layer 107 and second layer 108 can both be device wafers or more than the first layer 107 and second layer 108 can form the stacked wafer 102.

A light source 103 is configured to direct collimated light 104 at an edge of the stacked wafer 102. In some embodiments, the collimated light 104 is directed tangentially, with respect to the stacked wafer 102, so as to create a shadow of the edge profile. In an exemplary embodiment, the light source 103 utilizes a light-emitting diode (LED). Other suitable light sources 103, such as a lamp that produces collimated light, laser, supercontinuum laser, laser-driven phosphor, or laser-driven lamp, will be apparent in light of the present disclosure. Combinations of light sources 103, such as a laser and an LED, may be utilized. The light source 103 can include both single band and broadband light sources in a single system or multiple systems. The collimated light 104 is parallel to a plane of the stacked wafer 102. For example, the collimated light 104 may be parallel to the plane of the first layer 107 on which the second layer 108 is disposed. Diffraction suppression techniques may be used to remove diffraction-related artifacts that may adversely affect measurement of wafer thickness or other dimensions. Approximately a few millimeters of the stacked wafer 102 are seen in a profile using the collimated light 104, though other dimensions are possible.

A detector 105 located apart from the light source 103 receives at least some of the collimated light 104. The detector 105 is located such that when a stacked wafer 102 is under inspection, at least a portion of the shadow (i.e., the light producing the shadow) is received by the detector 105. The detector 105 can be, for example, a charge-coupled device (CCD) or complementary metal-oxide-semiconductor (CMOS) camera. In this way, an image of the wafer edge silhouette is formed. The detector 105 can be configured to collect hundreds of images on the stacked wafer 102 for high sampling. For example, between 1 and 500 images of the stacked wafer 102 may be collected, though more images can be collected. The images can be read and processed. In an example, metrology can be performed at hundreds of points along the edge of the stacked wafer 102 while the stacked wafer 102 is spinning up for inspection.

The collimated light 104 may have a wavelength or wavelengths that produce a shadow. For example, visible light such as blue light or white light may be used. Other suitable collimated light 104 will be apparent in light of the present disclosure. For example, ultraviolet light can be used. The collimated light 104 may be polarized and may be pulsed or continuous.

While only a single light source 103 and detector 105 are illustrated in FIGS. 1-3, multiple light sources 103 and detectors 105 may be used. Multiple light sources 103 and detectors 105 may be placed at various locations around the perimeter of the stacked wafer 102 to collect shadow-gram images at different locations of the stacked wafer 102. This may increase inspection throughput or increase the number of shadow-gram images produced while minimizing the impact to inspection throughput. If multiple light sources 103 and detectors 105 are placed at various locations around the perimeter of the stacked wafer 102, then the stacked wafer 102 may not rotate with respect to the light source 103 or detector 105.

A controller 106 is operatively connected to the detector 105. The controller 106 is configured to analyze a shadow-gram of the edge of the stacked wafer 102 and can control the acquisition of the shadow-gram images using the detector 105. For example, the controller 106 can rotate the stacked wafer 102 with respect to the light source 103 or detector 105. The controller 106 also can control the timing or locations of shadow-gram image acquisition on the stacked wafer 102. Using the shadow-gram, the system 100 can be used to evaluate the edge profile of the stacked wafer 102. For example, the system 100 may determine whether the edge profile of the stacked wafer 102 meets one or more pre-determined criteria, such as, for example, criteria related to the size of an inset width.

The system 100 can be an automated, inline system that can generate hundreds of inspection and measurement points at full scan throughput. The number of measurements can enable real-time statistical conclusions from the data. While one or only a few measurements may be sufficient, as the number of measurements increases, the better the data can provide conclusions for the entire stacked wafer 102. Inline algorithms can provide real-time feedback to other integrated inspection and review systems. For example, defective stacked wafers, such as those with stacking or glue problems, can be removed from manufacturing to either be re-worked or scrapped. In another example, a manufacturing step can be adjusted based on the conclusions from the data. For example, a CMP process or photoresist application process can be modified due to the conclusions from the data that is collected. The conclusions also can be used as feedback for the gluing, bonding, or stacking processes. Thus, these data or conclusions can be used as feedback for upstream or downstream processes of this inspection and metrology.

Figure 4:
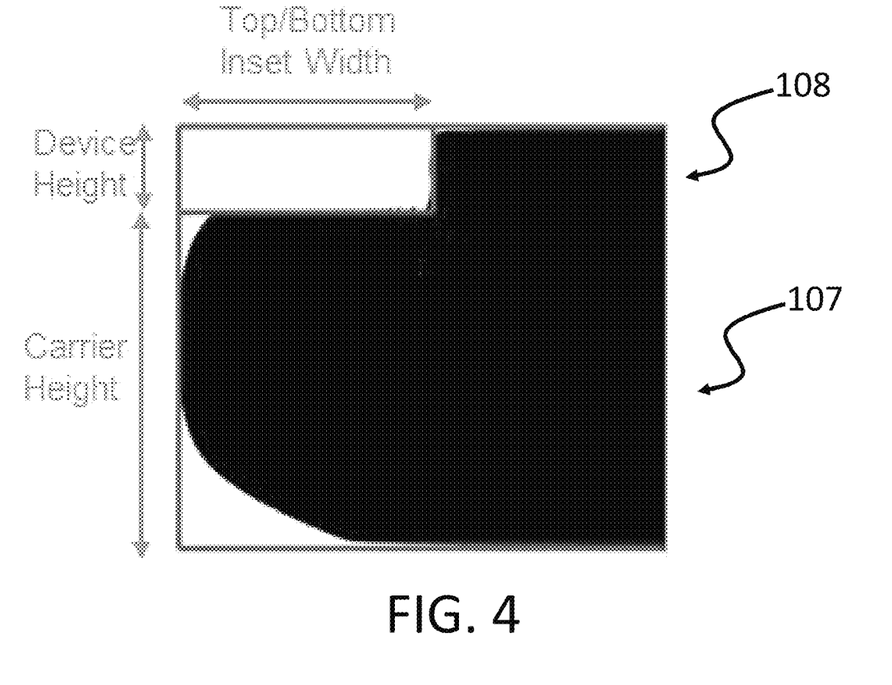
FIG. 4 is an exemplary shadow-gram profile of an edge of a stacked wafer.

FIG. 4 is an exemplary shadow-gram profile of an edge of a stacked wafer. The stacked wafer in FIG. 4 includes the first layer 107 and second layer 108. The first layer 107 is a carrier wafer and the second layer 108 is a device wafer in this instance. The edge profile of the stacked wafer in FIG. 4 may satisfy one set of exemplary desired measurements or characteristics.

Figure 5:
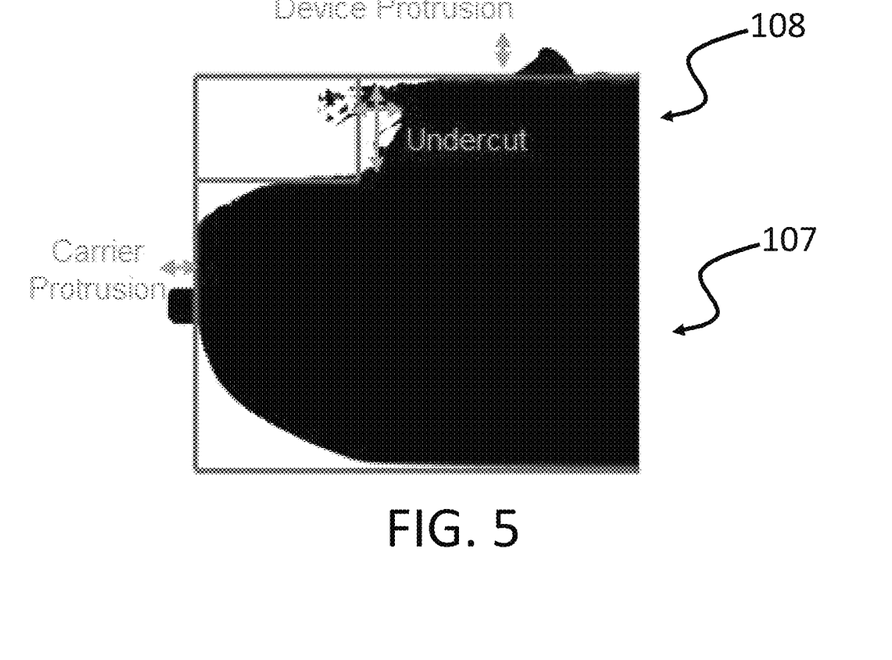
FIG. 5 is another exemplary shadow-gram profile of an edge of a stacked wafer.

FIG. 5 is another exemplary shadow-gram profile of an edge of a stacked wafer. The stacked wafer in FIG. 4 has undesirable profile characteristics. These undesirable profile characteristics include a device protrusion, a carrier protrusion, and an undercut.

Figure 6:
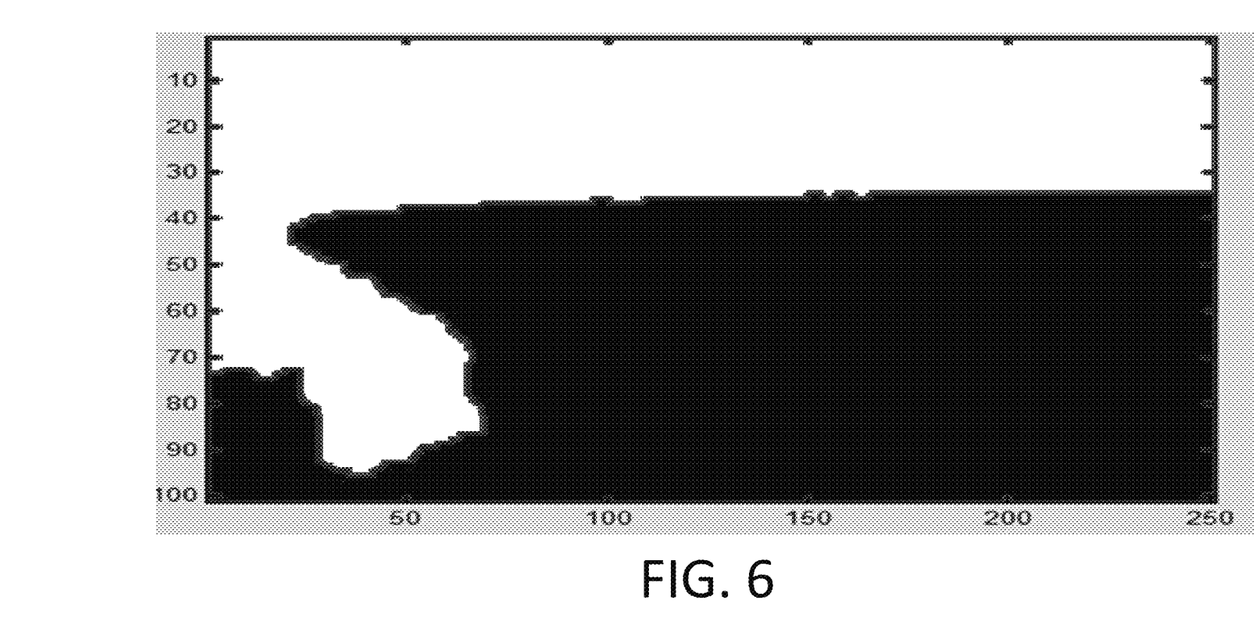
FIG. 6 is an exemplary shadow-gram edge profile with an undercut stacking fault.

FIG. 6 is another exemplary shadow-gram edge profile with an undercut stacking fault. The undercut can be a result of an etching process or other processing steps. The undercut region extends under part of the stacked wafer, such as under the device wafer or between a carrier wafer and a device wafer. An undercut stacking fault can affect yield of the stacked wafer or increase risk of stacked wafer breakage during a CMP process.

Figure 7:
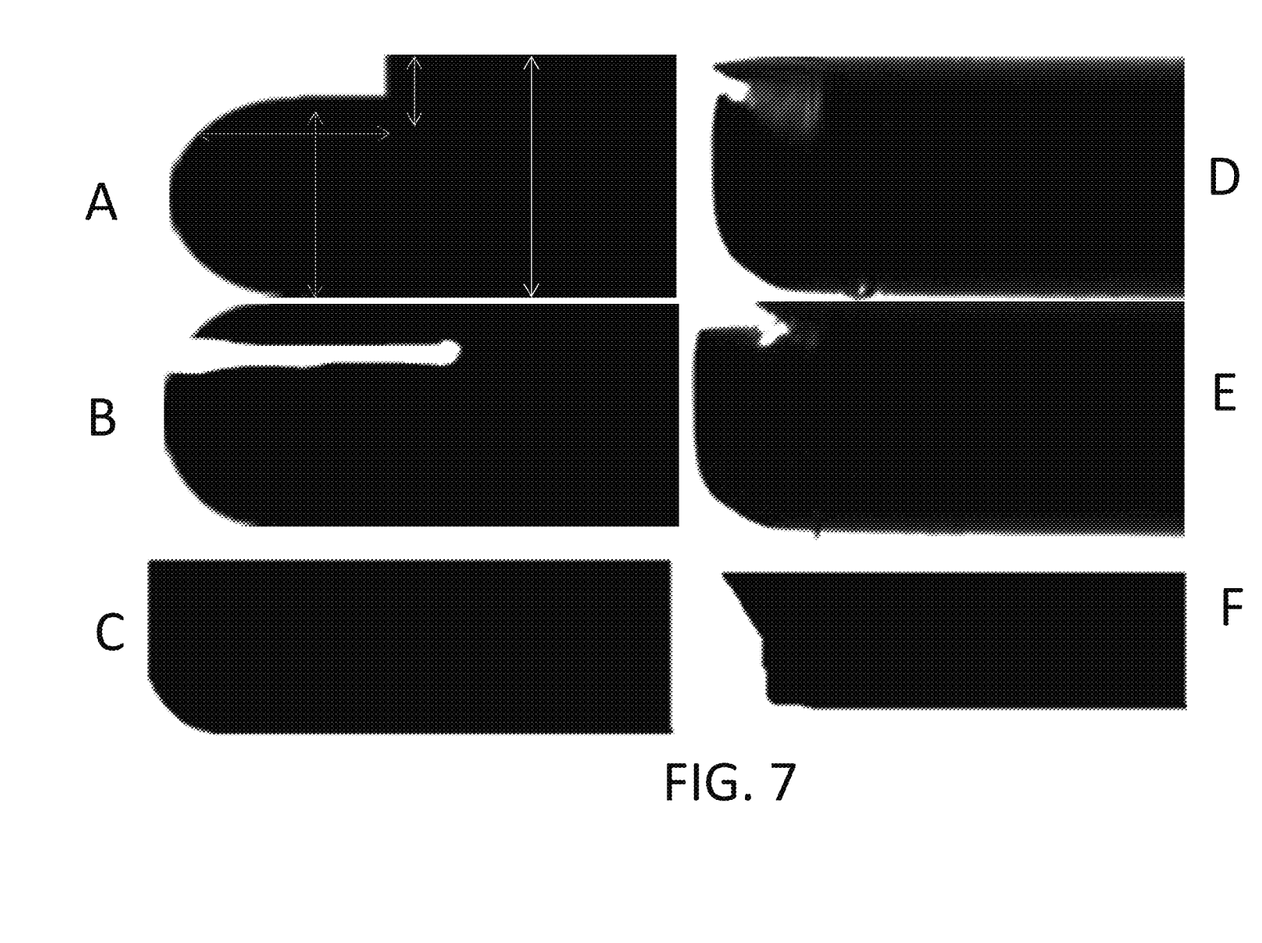
FIG. 7 is a series of exemplary shadow-gram profiles of different stacked wafers wherein stacked wafer A has an edge with desirable profile characteristics and stacked wafers B, C, D, E, and F have edges with undesirable profile characteristics.

FIG. 7 is a series of exemplary shadow-gram profiles of different stacked wafers. Stacked wafer A has desirable profile characteristics. Stacked wafers B, C, D, E, and F have undesirable profile characteristics. Stacked wafers B, D, and E have undercuts. Stacked wafer C and F may have both been incorrectly planarized in a CMP tool because too much material was removed from the stacked wafers C and F.

Figure 8:
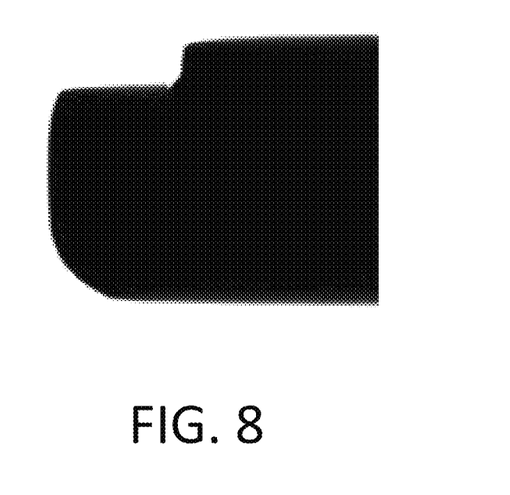
FIG. 8 is another exemplary shadow-gram profile of an edge of a stacked wafer with desirable profile characteristics.
Figure 9:
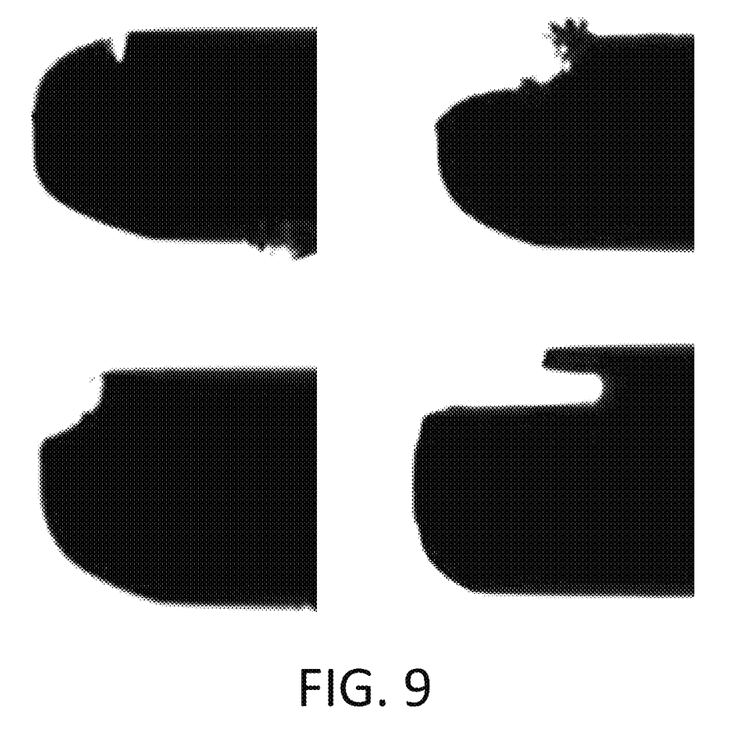
FIG. 9 are four exemplary shadow-gram profiles of stacked wafer edges with undesirable profile characteristics.

FIG. 8 is another exemplary shadow-gram profile of an edge of a stacked wafer with desirable profile characteristics. FIG. 9 are four exemplary shadow-gram profiles of stacked wafer edges with undesirable profile characteristics. The edge profiles in FIG. 8 include, for example, an undercut, whiskers, or improper dimensions.

Embodiments of the present disclosure may include systems and methods for automated metrology and/or inspection as well as the use of statistical information for inspection and review of a stacked wafer. In the above-described embodiment of a system 100, the controller 106 may be configured to analyze the edge profile of the stacked wafer 102 using methods such as those described below.

For example, edge extraction algorithms may be utilized as a first step to automate inspection of a stacked wafer's associated shadow-gram or shadow-grams. An edge extraction algorithm may identify attributes of a shadow-gram image that are significant to inspection such as corners, line segments, and curves in the shadow-gram. Many edge detection algorithms can be used such as, for example, search-based, zero-crossing based edge detection, and other morphological image processing methods. Search-based methods detect edges in an image, for example, by first computing a measure of edge strength. The measure of edge strength may be based on the discrete data in the image, for example, the color, hue, or brightness of a specific pixel of the image in relation to neighboring pixels. Edge strength may be measured by computing a first-order derivative expression of the image pixels such as the gradient magnitude of the image pixels. The pixels with the largest gradient values in the direction of the gradient (i.e., local directional maxima of the gradient magnitude) become edge pixels, and edges may be traced in the direction perpendicular to the gradient direction. One example of an edge detection algorithm that uses gradients is the Canny edge detector. Other edge detection algorithms may be used. In a Canny edge detector, four filters are used to detect horizontal, vertical and diagonal edges in the image. The edge detection calculations may return a value for the first derivative in the horizontal direction and the vertical direction. From this, the edge gradient and direction can be determined. In other words, the image may be mathematically analyzed to determine the areas in which the greatest changes in color, hue, or brightness occur (i.e., at the edge of a silhouette).

The zero-crossing based methods may search for zero crossings in a second-order derivative expression computed from the image pixels in order to find edges, for example, the zero-crossings of the Laplacian or the zero-crossings of a non-linear differential expression. For example, some edge-detection operators are based upon second-order derivatives of pixel intensity in the image. This essentially captures the rate of change in the intensity gradient. Thus, in a continuous case, detection of zero-crossings in the second derivative captures local maxima in the gradient.

As a pre-processing step to edge detection, a smoothing stage, for example, Gaussian smoothing, may be applied. Other types of smoothing stages may be applied. Edge detection may be affected by the noise from the image, so filtering out the noise may prevent some edge detection mistakes. For example, to smooth the image, a Gaussian filter may be applied to convolve with the image. This step may slightly smooth the image, so that it will not be significantly affected by separate obvious noise in the image. The larger the size of the filter, the lower is the edge detector's sensitivity to noise. Additionally, localization error to detect the edge may slightly increase with the increase of the size of Gaussian filter.

Other edge detection steps may be performed such as non-maximum suppression (comparing the edge strength of a pixel with the edge strength of pixels in the positive and negative gradient directions to determine if the current pixel has the largest edge strength and suppressing the others in the gradient), and thresholding (filtering out edge pixels with weak gradient values using a predetermined threshold value). Other alternative approaches can be used to detect a wafer profile edge in the shadow-gram image. Each approach may have its own unique advantages and disadvantages. For example, the shadow-gram image can be first transformed into a binary image by analyzing the histogram of the shadow-gram image. Connected component analysis may be utilized to remove erroneous external and internal blobs from the binary image. From the binary image a profile edge map can be detected by applying morphological perturbations.

After edge detection, chain code type algorithms are one of several options that may be used to mathematically describe the shadow-gram silhouettes. Other options may include edge tracking, classification methods based on specialized attributes, and intensity based segmentation algorithms. Chain code type algorithms may be used to represent a boundary by a connected sequence of straight-line segments of specified length and direction. The direction of each segment is coded by using a numbering scheme. For each connected component (i.e., each "blob" within an image), a point on the edge of the component may be selected and its coordinates may be recorded. The chain code algorithm may then moves along the edge and, at each step, records a value representing the direction of this movement. Typically, the direction value may be selected based on 4 directions (N, E, S, W), 8 directions, or more. The chain code of an edge may depend on the starting point. For example, starting at the left end of a segment may result in a different chain code than starting from the right end. However, the chain code may be normalized with respect to the starting point by treating it as a circular sequence of direction numbers and redefining the starting point so that the resulting sequence of numbers forms an integer minimum magnitude. Chain code algorithms can be used to separately encode each connected component in the silhouette.

An exemplary chain code algorithm records direction in relation to a two-dimensional set of coordinates. A chain code algorithm encodes the direction of travel of the edge into discrete directions and, in some embodiments, lengths. The chain code may be expressed using eight directions (i.e., N, NE, E, SE, S, SW, W, and NW or their equivalents on a two-dimensional set of coordinates). Other amounts of directions may be used, such as four directions (N, S, E, W) for quicker computation or sixteen (i.e., N, NNE, NE, ENE, E, ESE, SE, SSE, S, SSW, SW, WSW, W, WNW, NW, and NNW) and thirty-two direction chain code algorithms for higher resolution. Typically, chain code algorithms use numbers instead of letters to express the encoded direction. For example, in an eight-direction chain code algorithm, N=0, NE=1, E=2, SE=3, etc. Numbers are typically assigned in a clockwise fashion. In one embodiment, the recorded chain code values may be offset for mathematical convenience in implementation. In this way, using the previous example, N=1, NE=2, E=3, SE=4, etc. Offsetting the chain code values may be beneficial in order to avoid zero-based numbering mathematical computations.

The edge extraction algorithm may include segment generation from the recorded chain code values. For example, the chain code values may be represented in a matrix format such that the edge position (i.e., the pixels in the edge starting from the beginning point of the edge detection algorithm to the end of the edge) are on the x-axis and the chain codes values are on the y-axis, thus resulting in a binary matrix. Segments may be merged and deleted. For example, a bit-mask, such as a 1×3 binary mask (e.g., [111]) may be applied to the binary matrix to fill gaps in segments appearing in the binary matrix. Some segments may be deleted if the segment is below a certain threshold length. For example, the algorithm may parse each row of the binary matrix to find segment start and end points in order to calculate segment length. Segments with a length less than 20 pixels may be deleted.

Neighboring segments may be merged. For example, centroids of each segment may be calculated and compared with one another. For example, if the centroids of two compared segments are less than a specified number of pixels apart and the end-points are less than another specified number of pixels apart, the segments may be combined. In one embodiment, the specified number of pixels apart is 10 pixels. By completing these steps, small segments in the defect area of the stacked wafer can be eliminated and computation speed may be increased. Although segmentation can reduce resolution, the loss in resolution can be avoided by providing special attention to curved segment rows. For example, neighboring curved segments may be merged into a semi-circle or other general profile.

The edge extraction algorithm may also include measuring segments based on a known relationship between pixel size in the captured image and the stacked wafer. Measurements may be computed on one segment or on all segments. These computations may be performed in any order, or the computations may be performed by order of chain code direction. Appropriate pairs of measurements may be determined using centroid distance and segment independence.

Other approaches can include projection based algorithms where landmark locations between stacked wafer surfaces are determined by analyzing the edge trace points in the transition area between adjacent segments. Attributes such as local tangent angle to the edge trace, row-wise column-wise count of edge points, minimum radius of curvature along the points in the transition area can be used to accurately pinpoint key points of interested on the wafer under inspection. Once a set of required landmarks are detected, various metrology distances such as total height, device wafer height, carrier wafer height, inset width, undercut width/height, excess glue dimension (width/height/volume), etc. can be measured.

The acquired measurements may be compared to predetermined measurements, such as carrier height, device height, inset width, carrier height tolerance, device height tolerance, carrier edge protrusion threshold, and device edge protrusion threshold. These results may be displayed in a report or graphic user interface (GUI) to an operator. The results may be simplified as a "pass" or "fail" based on these comparisons.

The comparisons for each shadow-gram may be aggregated to provide wafer level statistics such as diameter, center offset, thickness, average total height, average device height, average carrier height, minimum goodness, maximum of all undercut heights, maximum of all undercut widths, maximum of device edge protrusion, maximum of carrier edge protrusion below, and maximum carrier protrusion left.

The following is an exemplary embodiment of an edge inspection algorithm according to the present disclosure.

A. The edge extraction algorithm receives or retrieves one or more shadow-gram images of the stacked wafer. The received or retrieved images may be in a file format readable by the algorithm and produced by an image capture device, such as the detector 105 in FIG. 1. The shadow-gram images may be taken from various locations on the circumference of the stacked wafer. The edge extraction algorithm opens the one or more images. Each image may be manipulated before edge extraction. For example, the image may be flipped horizontally or vertically based on the positioning of the detector. Other manipulations may be performed, such as adjusting the contrast of the image or applying various filters to remove noise from the image.

B. The edge extraction algorithm detects the edge of the stacked wafer silhouette. In one embodiment, the pixels of each image may be analyzed. An attribute of each pixel, such as color, brightness, or hue may be normalized such that each attribute lies in a scale from 0-100. The image can be "thresholded" by selecting a pixel value of either 0 or 1 based on the normalized attribute.

C. The edge extraction algorithm performs morphological operations on the image. In some embodiments, erosion and/or dilation may be performed on the image. For example, a bit-mask, such as a 3×3 bit mask $$\left( \begin{bmatrix} 1 & 1 & 1 \\ 1 & 1 & 1 \\ 1 & 1 & 1 \end{bmatrix} \right),$$

may be applied. The bit-mask may be applied multiple times. The morphological operations may close gaps in detected edges by joining edges together. Short edges may be removed completely. The edge extraction algorithm also may fill in areas of the image that cannot be reached from the edge of the image. In this way, the edge extraction algorithm fills in holes and artifacts caused by the edge detection process.

D. The edge extraction algorithm may detect and encode the edge of the stacked wafer silhouette by, for example, using algorithms like a chain code algorithm. Once a chain code is determined for the edge of the silhouette, segments can be filtered out or joined together for each orientation encoded by the chain code. This can be done by creating a binary matrix, wherein one axis corresponds to the chain code value, and the other axis corresponds to a pixel of the edge starting from the beginning point of the edge detection algorithm to the end of the edge. In one embodiment, dilation may be performed to join segments that are separated by a distance of half a pixel. Centroids of the segments may be calculated and the segments may be merged. In one embodiment, the consecutive segments may be merged if they are less than 10 pixels apart in the x-axis or y-axis. The centroid of the merged segments may be recalculated and compared with the centroids of other segments.

E. The edge extraction algorithm may also include measuring segments based on a known relationship between pixel size in the captured image and the stacked wafer. Measurements may be computed on one segment or on all segments. Attributes such as local tangent slope, local curvature along the edge trace, count of edge points projected on horizontal and vertical axis may be used to determine key landmarks that mark transition of surfaces and bonding material (glue) in the stacked wafer. The acquired measurements may be compared to predetermined measurements, such as carrier height, device height, inset width, carrier height tolerance, device height tolerance, carrier edge protrusion threshold, and device edge protrusion threshold. These results may be displayed in a report or graphic user interface (GUI) to an operator. The results may be simplified as a "pass" or "fail" based on these comparisons.

Figure 10:
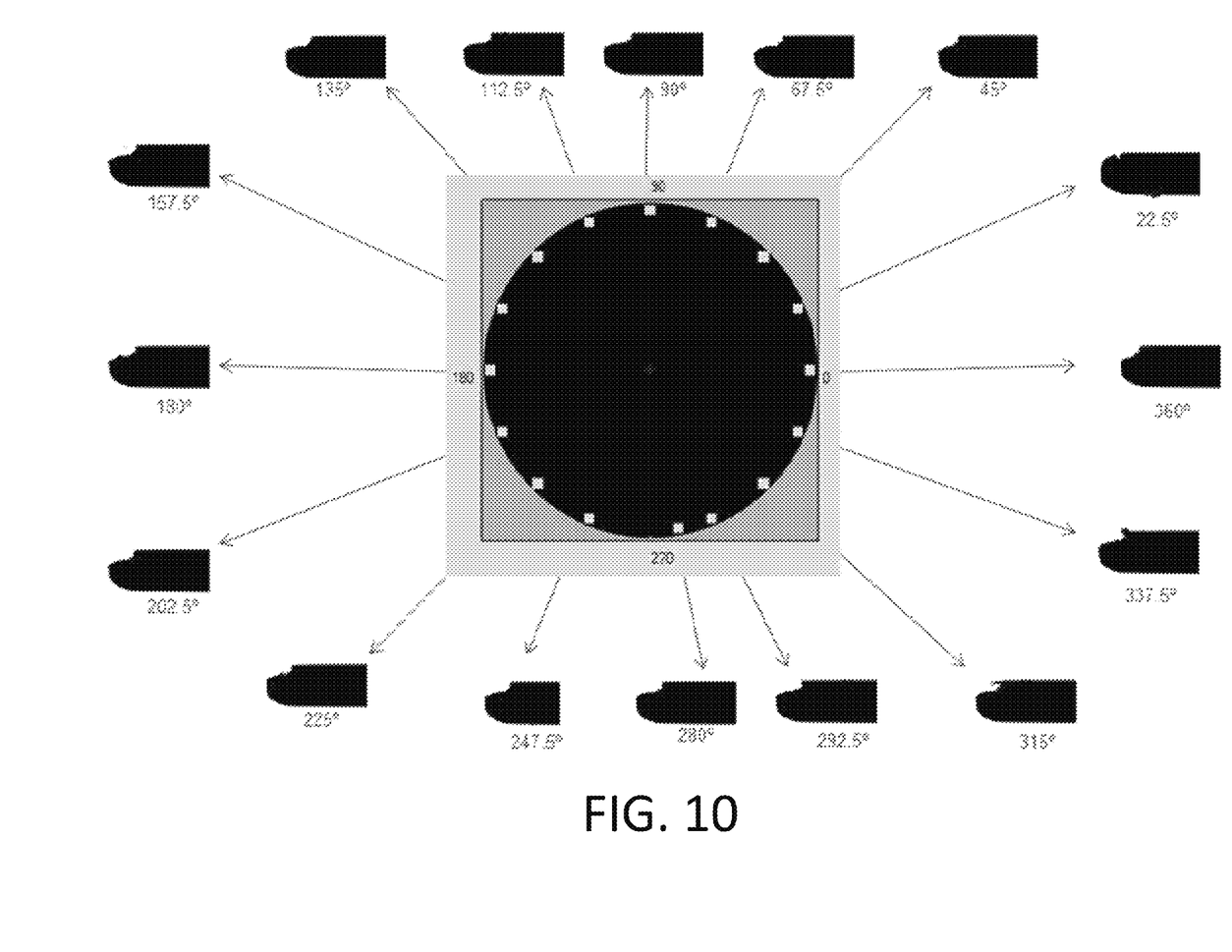
FIG. 10 is a series of exemplary shadow-gram edge profiles acquired around a perimeter of a stacked wafer.

Multiple shadow-gram images can be acquired for a single stacked wafer. FIG. 10 is a series of exemplary shadow-gram edge profiles acquired around a perimeter of a stacked wafer. While sixteen images are illustrated in FIG. 10, a user can select the number and placement of shadow-gram image acquisition locations. For example, shadow-grams may be acquired at hundreds of points around the perimeter of a stacked wafer at full scan throughput. The stacked wafer may rotate with respect to the light source or detector. For example, a controller, such as the controller 106 in FIG. 1, can acquire multiple images as the stacked wafer rotates on a platen. In the example of FIG. 10, inspection around the perimeter of the stacked wafer shows an improper profile at least at 22.5°, 315°, and 337.5°.

Figure 11:
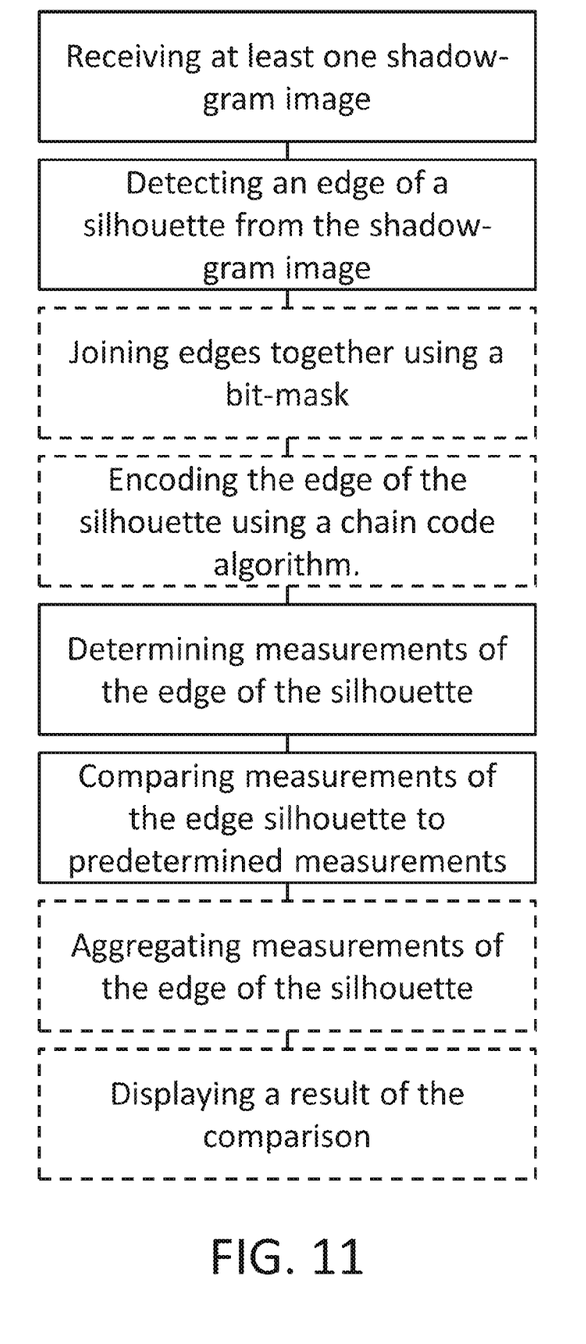
FIG. 11 is a flowchart of a method in accordance with an embodiment of the present disclosure.

FIG. 11 is a flowchart of a method in accordance with an embodiment of the present disclosure. Steps outlined in dotted lines may be optional.

The acquisition of shadow-gram images at multiple points on a single stacked wafer can provide additional or whole-wafer feedback. This can provide a more complete conclusion about the edge profile of a stacked wafer.

Centricity, bond characteristics, excess glue, undercut, whiskers, stacking angle, or other edge profile characteristics can be detected or measured using an embodiment of the present disclosure. Incorrectly stacked wafers can be identified before additional processing and can, for example, prevent damage to or contamination of a CMP tool or other manufacturing equipment. The inspection throughput of an embodiment of a system disclosed herein is high enough for a manufacturing setting. The stacked wafer can be irregular or can have complicated shapes, jagged edges, or high signal-to-noise, which was previously not possible to measure accurately or in a manufacturing setting. In fact, stacked wafers in which measurement was not previously possible can be measured using shadow-gram images as disclosed herein.

An embodiment of the present disclosure can determine or find stacked wafer errors or discrepancies that characterizes the gluing and bonding process. For example, wafer thickness, wafer concentricity, or profile information can be provided. Such information can be used as input in other inspection tools or other manufacturing or wafer handling tools.

Manufacturing throughput may not be affected or any impact to manufacturing throughput can be minimized using an embodiment of the present disclosure. The metrology and/or inspection process disclosed herein can be performed concurrently with other processes. For example, the metrology and/or inspection process disclosed herein can be performed during set-up of the inspection tool. Of course, the metrology and/or inspection process disclosed herein also can be performed separately as a stand-alone process.

A shadow-gram offers multiple advantages over bright field and dark field modes. For example, the shadow-gram receives sufficient signal from undercut type wafer stacking defects, which may not occur with bright field or dark field modes.

Although the present disclosure has been described with respect to one or more particular embodiments, it will be understood that other embodiments of the present disclosure may be made without departing from the scope of the present disclosure. Hence, the present disclosure is deemed limited only by the appended claims and the reasonable interpretation thereof.

What is claimed is:

1. A system comprising:
   a light source configured to tangentially direct collimated light at a circumferential edge of a stacked wafer, wherein the stacked wafer includes a first layer and a second layer disposed on top of the first layer;
   a detector disposed on an opposite side of the stacked wafer from the light source to receive at least some of the collimated light from the light source, wherein the detector is configured to acquire a shadow-gram image of the circumferential edge of the stacked wafer, wherein the shadow-gram image is configured to image a shadow of an edge profile of the first layer and the second layer of the stacked wafer by applying a shadowgraph technique; and
   a controller operatively connected to the detector, wherein the controller is configured to:
   receive the shadow-gram image; and
   compare characteristics of the shadow-gram image with predetermined measurements to inspect an edge profile of the stacked wafer.

2. The system of claim 1, wherein the detector is further configured to acquire a plurality of the shadow-gram images of different locations of the stacked wafer.

3. The system of claim 1, further comprising a platen configured to rotate the stacked wafer.

4. The system of claim 3, wherein the detector is configured to obtain a plurality of the shadow-gram images at different points along the circumferential edge of the stacked wafer while the stacked wafer is rotated.

5. The system of claim 1, wherein the stacked wafer is configured to rotate with respect to the light source.

6. The system of claim 1, wherein the shadow-gram image includes a silhouette, and wherein the controller is further configured to compare measurements of the silhouette of the stacked wafer in the shadow-gram image to the predetermined measurements.

7. The system of claim 6, wherein the controller is further configured to aggregate the measurements of the silhouette in a plurality of the shadow-gram images such that information for the stacked wafer is provided.

8. The system of claim 1, wherein the light source includes an LED.

9. The system of claim 1, wherein the detector includes at least one of a CCD or CMOS camera.

10. The system of claim 1, wherein the collimated light is one of visible light or UV light.

11. The system of claim 1, wherein the light source is configured to provide pulsed collimated light.

12. The system of claim 1, further comprising a plurality of the light sources and a plurality of the detectors.

13. The system of claim 1, wherein the controller is configured to use at least one edge extraction algorithm to measure the characteristics of the edge profile of the stacked wafer.

14. The system of claim 1, wherein the controller is configured to apply smoothing to the shadow-gram image.

15. The system of claim 1, wherein the controller is configured to use a chain code type algorithm to describe the shadow-gram image.

* * * * *